United States Patent
Choi et al.

(10) Patent No.: US 11,866,447 B2
(45) Date of Patent: Jan. 9, 2024

(54) REACTIVE DEASPHALTING PROCESS

(71) Applicant: Saudi Arabian Oil Company, Dhahran (SA)

(72) Inventors: Ki-Hyouk Choi, Dhahran (SA); Mohammad Saeed Garhoush, Dhahran (SA); Tariq Abdullah Khathami, Dhahran (SA); Obied Abdulrahman Alotaibi, Dhahran (SA); Mohammed Saad Aldossary, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 206 days.

(21) Appl. No.: 17/591,670

(22) Filed: Feb. 3, 2022

(65) Prior Publication Data
US 2023/0242549 A1 Aug. 3, 2023

(51) Int. Cl.
C07D 495/22 (2006.01)
B01D 17/02 (2006.01)
B01J 19/00 (2006.01)
B01J 19/24 (2006.01)
B01D 19/00 (2006.01)

(52) U.S. Cl.
CPC ............ *C07D 495/22* (2013.01); *B01D 17/02* (2013.01); *B01D 19/0068* (2013.01); *B01J 19/0006* (2013.01); *B01J 19/0013* (2013.01); *B01J 19/242* (2013.01); *B01J 19/2415* (2013.01); *B01J 2219/0004* (2013.01); *B01J 2219/00051* (2013.01); *B01J 2219/00162* (2013.01)

(58) Field of Classification Search
CPC ...... C07D 495/22; B01D 17/02; B01J 19/006; B01J 19/0013; B01J 19/2415; B01J 19/242
See application file for complete search history.

(56) References Cited

U.S. PATENT DOCUMENTS

| | | | |
|---|---|---|---|
| 7,264,710 | B2 | 9/2007 | Hokari et al. |
| 9,670,419 | B2 | 6/2017 | Choi et al. |
| 9,957,450 | B2 | 5/2018 | Choi et al. |
| 10,066,172 | B2 | 9/2018 | Choi et al. |
| 10,584,285 | B2 | 3/2020 | Choi et al. |
| 10,920,152 | B2 | 2/2021 | Snow et al. |
| 10,995,281 | B2 | 5/2021 | Choi et al. |
| 11,021,659 | B2 | 6/2021 | Choi et al. |
| 11,118,121 | B2 | 9/2021 | Fathi et al. |
| 2008/0099374 | A1 | 5/2008 | He et al. |
| 2014/0109465 | A1 | 4/2014 | Coppola et al. |
| 2018/0037828 | A1 | 2/2018 | Choi et al. |

FOREIGN PATENT DOCUMENTS

EP 1489046 A1 12/2004

OTHER PUBLICATIONS

Ashtari et al., "New Pathways for Asphaltenes Upgrading Using the Oxy-Cracking Process", Energy Fuels, 2016, 30, pp. 4596-4608.
Choi et al., "Asphaltene precipitation with partially oxidized asphaltene from water/heavy crude oil emulsion", Journal of Petroleum Science and Engineering, 146, 2016, pp. 21-29.

*Primary Examiner* — Sikarl A Witherspoon
(74) *Attorney, Agent, or Firm* — Bracewell LLP; Constance G. Rhebergen; Eleanor T. Porter

(57) ABSTRACT

A method to convert asphaltenes to partially oxidized asphaltenes comprising the steps of treating the reactor feed in a tubular reactor to produce a reactor effluent, introducing the reactor effluent to a disengagement zone of a vessel reactor, introducing an oxidizing agent stream to the asphaltene collection zone of the vessel reactor, reacting the asphaltenes in the asphaltene-rich fraction with oxygen from the oxidizing agent, withdrawing a bottom reactor effluent from the asphaltene collection zone, reducing a temperature of the bottom reactor effluent to produce a cooled bottom effluent, reducing a pressure of the cooled bottom effluent in a pressure regulator unit to produce a centrifuge feed, separating the centrifuge feed in a centrifuge to produce a centrate, mixing the centrate and the upper upgraded stream in a product mixer to produce a mixed upgraded stream, and separating the mixed upgraded stream in a three-phase separator.

18 Claims, 2 Drawing Sheets

REACTIVE DEASPHALTING PROCESS

TECHNICAL FIELD

Disclosed are methods for upgrading petroleum. Specifically, disclosed are methods and systems for upgrading petroleum by converting and separating asphaltenes.

BACKGROUND

The asphaltene fraction, which is generally defined as the fraction having poor solubility in a paraffinic solvent, such $C_3$-$C_7$ paraffinic solvent, is concentrated in the bottom fraction of crude oil. Due to its high content of impurities, such as sulfur, nitrogen, and metals, boiling point greater than 500° C., and high viscosity, conventional refining process cannot upgrade asphaltene fractions to lighter and cleaner non-asphaltene fractions without rejecting substantial portions of it to much lower valued products, for example solid coke, or adopting high severity upgrading process, such as high pressure slurry hydrocracking. Thus, the asphaltene fraction plays a key limiting factor in increasing liquid product yield while maintaining quality of the product in a refining process.

SUMMARY

Disclosed are methods for upgrading petroleum. Specifically, disclosed are methods and systems for upgrading petroleum by converting and separating asphaltenes.

In a first aspect, a method to convert asphaltenes to partially oxidized asphaltenes is provided. The method includes the steps of increasing a pressure of a feedstock in a feedstock pump to produce a pressurized feedstock, where the feedstock includes greater than 0.1 weight percent of carbon 7-asphaltene (C7-asphaltene) content, increasing a temperature of the pressurized feedstock in a feedstock heater to produce a heated feedstock, increasing a pressure of a water stream in a water pump to produce a pressurized water stream, increasing a temperature of the pressurized water stream in a water heater to produce a supercritical water, mixing the heated feedstock and the supercritical water in a feed mixer to produce a mixed feed, where a temperature of the mixed feed is between 100° C. and 400° C., and increasing a temperature of the mixed feed in a pre-heater to produce a reactor feed. The method further includes the step of treating the reactor feed in a tubular reactor to produce a reactor effluent, where the tubular reactor includes one or more pipes in series, where the temperature in the tubular reactor is between 374° C. and 500° C., where the pressure is between 220 barg and 330 barg, where the residence time is between 0.5 minutes and 30 minutes. The method further includes the steps of introducing the reactor effluent to a disengagement zone of a vessel reactor, where an asphaltene-rich fraction disengages from a non-asphaltene fraction and flows to an asphaltene collection zone of the vessel reactor, where the disengagement zone is positioned at a greater elevation than the asphaltene collection zone, where the asphaltene-rich fraction includes asphaltenes, introducing an oxidizing agent stream to the asphaltene collection zone of the vessel reactor, where the oxidizing agent stream includes an oxidizing agent and water, and reacting the asphaltenes in the asphaltene-rich fraction with oxygen from the oxidizing agent to produce partially oxidized asphaltenes, where a temperature in the vessel reactor is in the range between 374° C. and 500° C., where a pressure in the vessel reactor is between 220 barg and 330 barg. The method further includes the steps of withdrawing an upper reactor effluent from the disengagement zone, withdrawing a bottom reactor effluent from the asphaltene collection zone, reducing a temperature of the upper reactor effluent in an upper cooler to produce a cooled upper effluent, where the temperature of the cooled upper effluent is between 50° C. and 150° C., reducing a pressure of the cooled upper effluent in a pressure control unit to produce an upper upgraded stream, where the pressure of the upper upgraded stream is between 1 barg and 5 barg, reducing a temperature of the bottom reactor effluent in a bottom cooler to produce a cooled bottom effluent, where the temperature of the cooled bottom effluent is between 70° C. and 150° C., reducing a pressure of the cooled bottom effluent in a pressure regulator unit to produce a centrifuge feed, where the pressure of the centrifuge feed is between 1 barg and 5 barg, separating the centrifuge feed in a centrifuge to produce a centrate and a rejected phase, where the temperature in the centrifuge is between 20° C. and 90° C., where the rejected phase includes flocculated asphaltenes, where the flocculated asphaltenes include partially oxidized asphaltenes, mixing the centrate and the upper upgraded stream in a product mixer to produce a mixed upgraded stream, and separating the mixed upgraded stream in a three-phase separator to a produce gas product, an upgraded oil product, and a water product.

In certain aspects, a temperature of the heated feedstock is between between 100° C. and 250° C. and a pressure is between 220 barg and 330 barg. In certain aspects, a temperature of the supercritical water is between 374° C. and 600° C. and a pressure is between 220 barg and 330 barg. In certain aspects, the oxidizing agent is selected from the group consisting of hydrogen peroxide, organic peroxide, oxygen gas, air, or combinations of the same. In certain aspects, the tubular reactor includes 4 pipes in series. In certain aspects, a flow rate of oxidizing agent stream is such that an amount oxygen is in the range of 10% to 300% of the mass amount of C7-asphaltene content. In certain aspects, the total volume of the vessel reactor is equal to 0.1 to 1 times the volumetric flow rate of the reactor effluent. In certain aspects, the ratio of the volume of the disengagement zone to the volume of the asphaltene collection zone is between 1:1 and 10:1. In certain aspects, the ratio of the diameter of the disengagement zone to the volume of the asphaltene collection zone is between 2:1 and 5:1.

In a second aspect, a system to convert asphaltenes to partially oxidized asphaltenes is provided. The system includes a feedstock pump configured to increase a pressure of a feedstock to produce a pressurized feedstock, where the feedstock includes greater than 0.1 weight percent of carbon 7-asphaltene (C7-asphaltene) content, a feedstock heater fluidly connected to the feedstock pump, the feedstock heater configured to increase a temperature of the pressurized feedstock to produce a heated feedstock, a water pump configured to increase a pressure of a water stream to produce a pressurized water stream, a water heater fluidly connected to the water pump, the water heater configured to produce a supercritical water, a feed mixer fluidly connected to the feedstock heater and the water heater, the feed mixer configured to mix the heated feedstock and the supercritical water to produce a mixed feed, where the feed mixer is selected from the group consisting of an ultrasonic device, agitator-equipped vessel, and a tee fitting, a pre-heater fluidly connected to the feed mixer, the pre-heater configured to produce a reactor feed, a tubular reactor fluidly connected to the pre-heater, the tubular reactor configured to produce a reactor effluent, where the tubular reactor includes one or more pipes in series, where the tubular reactor has a residence time between 0.5 minutes and 30 minutes, a vessel reactor fluidly connected to the tubular reactor, the vessel reactor configured to produce an upper reactor effluent and a bottom reactor effluent, where the vessel reactor includes a disengagement zone and an asphaltene collection zone, where the disengagement zone is positioned at a greater elevation than the asphaltene collection zone, where a distributer in the asphaltene collection zone is configured to distribute oxidizing agent stream into the asphaltene collection zone, where the oxidizing agent stream includes oxidizing agent and water, an upper cooler fluidly connected to the disengagement zone, the upper cooler configured to produce a cooled upper effluent, a pressure control unit fluidly connected to the upper cooler, the pressure control unit configured to produce an upper upgraded stream, a bottom cooler fluidly connected to the asphaltene collection zone, the bottom cooler configured to produce a cooled bottom effluent, a pressure regulator unit fluidly connected to the bottom cooler, the pressure regulator unit configured to produce a centrifuge feed, a centrifuge fluidly connected to the pressure regulator unit, the centrifuge configured to produce a centrate and a rejected phase, a product mixer fluidly connected to the pressure control unit and the centrifuge, the product mixer configured to mix the upper upgraded stream and the centrate to produce a mixed upgraded stream, and a three-phase separator fluidly connected to the product mixer, the three-phase separator configured to produce a gas product, an upgraded oil product, and a water product.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

DETAILED DESCRIPTION

Figure 1:
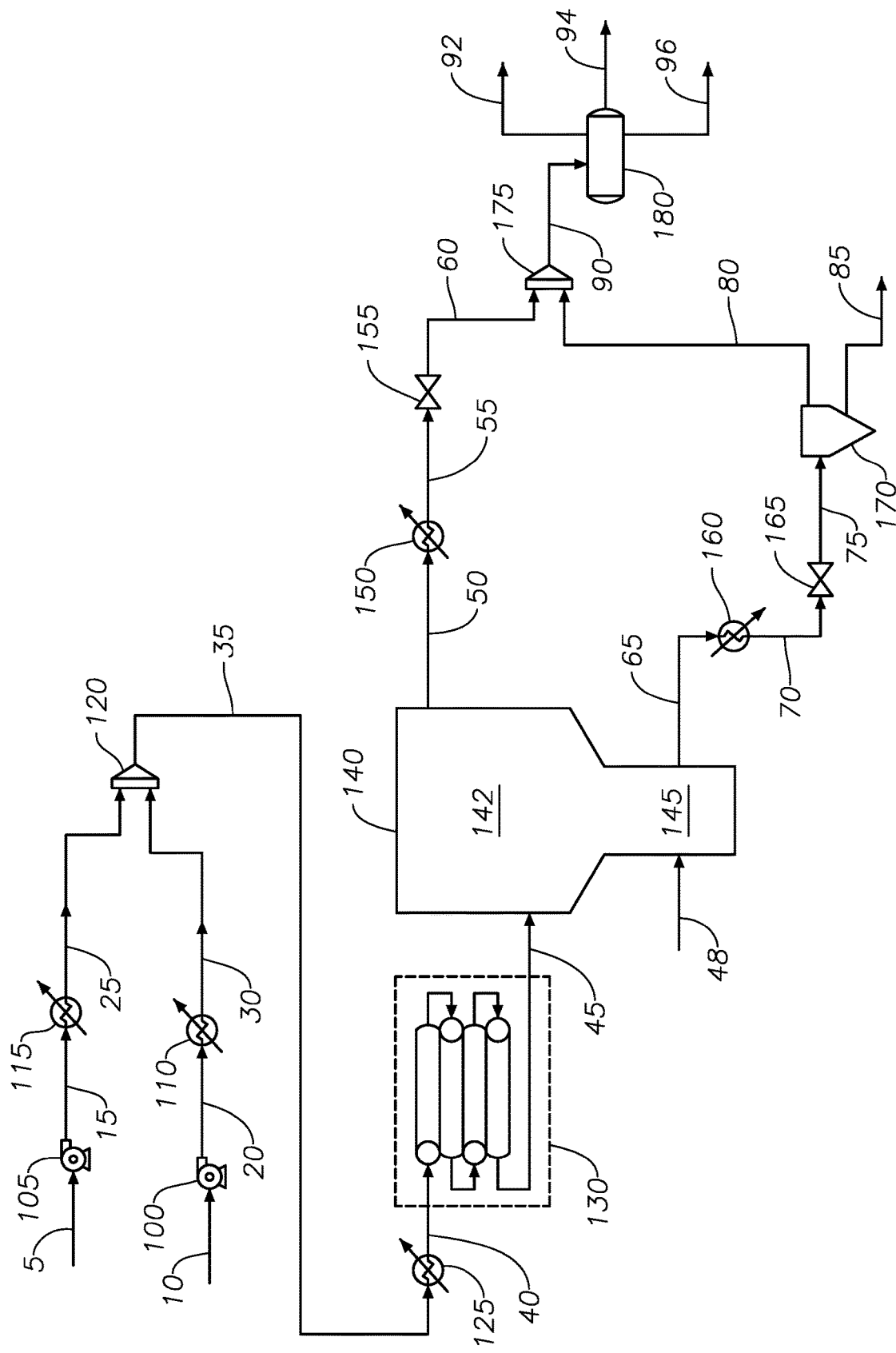
FIG. 1 provides a process diagram of an embodiment of the process.

While the scope will be described with several embodiments, it is understood that one of ordinary skill in the relevant art will appreciate that many examples, variations and alterations to the apparatus and methods described herein are within the scope and spirit. Accordingly, the embodiments described are set forth without any loss of generality, and without imposing limitations, on the embodiments. Those of skill in the art understand that the scope includes all possible combinations and uses of particular features described in the specification.

Described here are processes and systems for the conversion and separation of asphaltene fractions in crude oil. The processes and systems described here utilize water as a reaction and separation medium along with oxidation reaction. More specifically, the asphaltene-rich fraction is selectively disengaged from the non-asphaltene fraction due to solubility differences of those fractions in supercritical water. The asphaltene-rich fraction is then subjected to oxidation reaction followed by a separation step. The processes and systems described can effectively disengage the asphaltene-rich fraction in the vessel reactor and gather the disengaged asphaltene-rich fraction in the bottom part of the vessel reactor. Gathering the asphaltene-rich fraction in the bottom part of the vessel reactor selectively exposes the asphaltene-rich fraction to the oxidizing agent, while minimizing exposure of the non-asphaltene fraction to the oxidizing agent. The processes and systems described can control the extent of oxidation resulting in partial oxidation, where total oxidation to carbon monoxide and carbon dioxide production is suppressed. The partial oxidation is the mechanism through which the asphaltene-rich fraction is upgraded and separated, because the partially oxidized asphaltenes are lighter than the un-oxidized asphaltenes. The processes and systems utilize supercritical water as an extraction medium.

Advantageously and unexpectedly, the processes and systems described here result in an upgraded oil product that contains increased non-asphaltene fractions, increased light fractions, and reduced amounts of impurities compared to conventional upgrading processes. Advantageously and unexpectedly, the processes and systems described allow the asphaltene fraction to be disengaged from the non-asphaltene fraction, which disengaged asphaltene fraction can then be subjected to oxidation reactions. Advantageously, supercritical water is a good medium for oxidation reactions because oxygen is fully miscible in supercritical water. Advantageously, the vessel reactor of the processes and systems described allows for partial oxidation of asphaltenes which results in upgrading the asphaltenes and producing a flocculating agent. Advantageously and unexpectedly, a centrifuge can be used to separate flocculated asphaltenes. Advantageously and unexpectedly, the systems and processes allow for upgrading and separating asphaltene by a single process.

As used throughout, "asphaltenes" refers to a mix of high molecular weight polycyclic aromatic hydrocarbons, which consist primarily of carbon, hydrogen, nitrogen, oxygen and sulfur with trace amounts of metals such as vanadium and nickel, and a hydrogen to carbon ratio of about 1.2 to 1. Operationally, asphaltenes refers to the n-heptane-insoluble, toluene soluble component of a carbonaceous material. Asphaltenes are the sticky, black, highly viscous residue of distillation processes. Asphaltenes contain highly polar species that tend to associate or aggregate, which has made complete molecular analysis of asphaltenes, for example by mass spectrometry, difficult.

As used throughout, "upgraded hydrocarbon" means a hydrocarbon with one or all of increased API gravity, decreased amount of impurities, such as sulfur, nitrogen, and metals, decreased amount of asphaltene, and increased amount of distillate relative to the hydrocarbon in process feed stream. One of skill in the art understands that upgraded hydrocarbons can have a relative meaning such that a stream of upgraded hydrocarbons can be upgraded in comparison to another stream of hydrocarbons, but can still contain undesirable components such as impurities.

As used throughout, "externally supplied" refers to any source of material not part of the feed streams to a process or a system. Externally supplied does not encompass those materials inherent in the feedstock.

As used throughout, "absence of" means does not contain, does not include, does not comprise, is without, or does not occur.

As used throughout, "flocculated asphaltenes" refers to partially oxidized asphaltenes that have aggregated as defined in Seonung Choi, Do Hyun Byun, Kwangse Lee, Jong-Duk Kima, Nam Sun Nho, "*Asphaltene precipitation with partially oxidized asphaltene from water/heavy crude oil emulsion*", Journal of Petroleum Science and Engineering, 146, 2016, Pages 21-29.

In supercritical water as a reaction medium, most of the hydrocarbons found in crude oil can be dissolved and eventually form a single phase with supercritical water. However, the asphaltene-rich fraction, which is heavy and even polar, cannot be readily dissolved in supercritical water and eventually forms a denser and separated phase. This means a supercritical water reactor can be utilized as a reactive extraction unit.

Certain chemical bonds of the asphaltene-rich fraction are vulnerable to oxidation to form carbon monoxide, carbon dioxide, and oxygenated hydrocarbons. By controlling the oxidizing agent amount, amount of oil, temperature, pressure, and residence time, the total oxidation to carbon monoxide and carbon dioxide can be minimized. The products of partial oxidation of the asphaltene fraction can include carboxylic acid, aldehyde, ketone compounds, alcohol compounds, and combinations of the same. Some of the asphaltene fraction acquires oxygen on it to form oxygen-containing asphaltene. Oxidation can convert a solvent-insoluble fraction to solvent soluble fraction by producing lighter hydrocarbons. But, some part of partially oxidized asphaltene still remains as a solvent-insoluble with increased oxygen content. Other than forming oxygenates, partial oxidation of asphaltene fraction can induce cracking of asphaltene, meaning lowering of molecular weight and reducing the size of asphaltenes.

With reference to FIG. 1, a process flow diagram for the process to convert asphaltene is provided.

Feedstock 10 is transferred to feedstock heater 110 through feedstock pump 100. Feedstock 10 can be any source of hydrocarbons containing an asphaltene fraction. Feedstock 10 can contain greater than 0.1 weight percent (wt %) of carbon 7-($C_7$) asphaltenes content, alternately greater than 0.5 wt % of C7-asphaltenes content, and alternately between 1 wt % and 10 wt % of C7-asphaltenes content. C7-asphaltene content is measured by n-heptane insoluble fraction under ASTM D-3279. Feedstock 10 has an API gravity less than 36 and alternately less than 32. Examples of hydrocarbons include whole range crude oil, petroleum crude oil fractions, refining streams, liquefied coal fractions, liquefied biomass fractions, liquefied plastics, and combinations of the same.

Feedstock pump 100 can increase the pressure of feedstock 10 to produce pressurized feedstock 20. Feedstock pump 100 can be any type of pump capable of increasing the pressure of a hydrocarbon stream. In at least one embodiment, feedstock pump 100 is a diaphragm metering pump. The pressure of pressurized feedstock 20 can be greater than the critical pressure of water, alternately between 220 bar gauge (barg) and 330 barg and alternately between 230 barg and 300 barg.

Feedstock heater 110 can increase the temperature of pressurized feedstock 20 to produce heated feedstock 30. Feedstock heater 110 can be any type of heat exchanger capable of increasing the temperature of a hydrocarbon stream. Examples of feedstock heater 110 can include heat exchanger, electric heater, gas fired heater, and oil fired heater. The temperature of heated feedstock 30 is less than 250 degrees Celsius (° C.) and alternately between 100° C. and 250° C.

Water stream 5 is transferred to water heater 115 through water pump 105. Water stream 5 can be any demineralized water. Water stream 5 has a conductivity less than 1.0 microSiemens per centimeter (µS/cm), alternately less than 0.5 µS/cm, and alternately less than 0.1 µS/cm. Water stream 5 has a sodium content less than 5 microgram per liter (µg/l) and alternately less than 1 µg/l. Water stream 5 has a chloride content less than 5 µg/l and alternately less than 1 µg/l. Water stream 5 has a silica content less than 3 µg/l. The ratio of the mass flow rate of feedstock 10 to the mass flow rate of water stream 5 is between 10:1 and 1:10 and alternately between 2:1 and 1:4.

Water pump 105 can increase the pressure of water stream 5 to produce pressurized water stream 15. Water pump 105 can be any type of pump capable of increasing the pressure of a water stream. In at least one embodiment, water pump 105 is a diaphragm metering pump. The pressure of pressurized water stream 15 can be greater than the critical pressure of water, alternately between 220 barg and 330 barg and alternately between 230 barg and 300 barg.

Water heater 115 can increase the temperature of pressurized water stream 15 to produce supercritical water 25. Water heater 115 can be any type of heat exchanger capable of increasing the temperature of a water stream. Examples of water heater 115 can include heat exchanger, electric heater, gas fired heater, and oil fired heater. The temperature of supercritical water 25 can be between the critical temperature of water and 600° C. and alternately between 450° C. and 500° C.

Supercritical water 25 and heated feedstock 30 are introduced to feed mixer 120 to produce mixed feed 35. Feed mixer 120 can be any type of mixing device capable of mixing supercritical water 25 and heated feedstock 30. Examples of feed mixer 120 can include an ultrasonic device, agitator-equipped vessel, and a tee fitting. Feed mixer 120 allows for thorough mixing of water and the hydrocarbons in heated feedstock 30. The temperature of mixed feed 35 can be less than 400° C. and alternately between 100° C. and 400° C. Mixed feed 35 can be introduced to pre-heater 125.

Pre-heater 125 can increase the temperature of mixed feed 35 to produce reactor feed 40. Pre-heater 125 can be any type of heat exchanger capable of increasing the temperature of a mixed water and hydrocarbon stream. The temperature of reactor feed 40 can be in the range of 5° C. to 50° C. less than the temperature in tubular reactor 130. In addition to increasing the temperature of mixed feed 35, pre-heater 125 enhances the mixing of hydrocarbons and supercritical Tubular reactor 130 can be one or more pipes in series. The number and size of pipes in tubular reactor 130 depends on the flow rate, reaction conditions, and spatial restrictions. As shown in FIG. 1, four pipes in series are used. The individual pipes in tubular reactor 130 can be arranged in vertical, horizontal, inclined, declined, helical, or any combination of the same. Fluid can flow upward, downward, or any combination. The residence time in tubular reactor 130 is between 0.5 minutes and 30 minutes and alternately between 1 minute and 10 minutes. One of skill in the art understands that the residence time is calculated based on the overall length of all pipes in tubular reactor 130. The residence time is calculated by assuming the internal fluid is 100% water. In addition to upgrading reactions occurring in tubular reactor 130, tubular reactor 130 facilitates mixing of hydrocarbons and supercritical water using fluid turbulence by maintaining Reynolds numbers greater than 3,000 and alternately greater than 6,000. The temperature in tubular reactor 130 can be in the range of 374° C. and 500° C. and alternately between 400° C. and 460° C. The temperature in each pipe of tubular reactor 130 can be the same or each can be different so long as each pipe is within the overall range of 374° C. and 500° C. and alternately between 400° C. and 460° C. The pressure in tubular reactor 130 can be in the range between alternately between 220 barg and 330 barg and alternately between 230 barg and 300 barg. Reactions in tubular reactor 130 can include cracking reactions, isomerization reactions, dehydrogenation reactions, cyclization reactions, aromatization reactions, dimerization reactions, desulfurization reactions, denitrogenation reactions, demetallization reactions, deoxygenation reactions, and combinations of the same. The primary reaction that occurs in tubular reactor 130 is cracking reactions. Dealkylation reactions, a type of cracking reactions, also occur.

Figure 2:
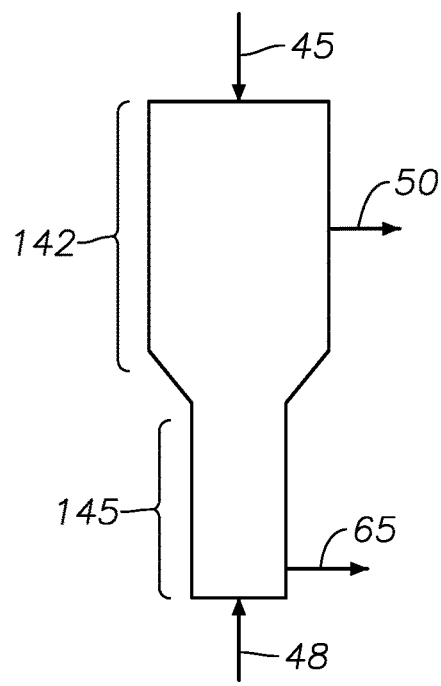
FIG. 2 provides a process diagram of an embodiment of the vessel reactor.

Reactor effluent 45 can be introduced to vessel reactor 140. In at least one embodiment, reactor effluent 45 is introduced to the top or middle of vessel reactor 140. Referring to FIG. 2, vessel reactor 140 can be any type of vessel-type reactor that contains two zones: disengagement zone 142 and asphaltene collection zone 145. The temperature in vessel reactor 140 can be in the range between 374° C. and 500° C. and alternately between 400° C. and 460° C. The total volume of vessel reactor 140 is based on the volumetric flow rate of reactor effluent 45, as measured at a rate of volume per hour. The total volume of vessel reactor 140 is equal to 0.1 to 1 times the volumetric flow rate of reactor effluent 45. The ratio of the volume of disengagement zone 142 to the volume of asphaltene collection zone 145 is between 1:1 and 10:1. The ratio of the diameter of disengagement zone 142 to the volume of asphaltene collection zone 145 is between 2:1 and 5:1.

In disengagement zone 142, the asphaltene-rich fraction separates from the non-asphaltene fraction of reactor effluent 45. Reduced fluid velocity in disengagement zone 142 allows the denser asphaltene-rich fraction to separate from the other fraction. The separated fraction primarily consists of the asphaltene-rich fraction and supercritical water fraction. This denser asphaltene-rich fraction flows downward into the bottom of vessel reactor 140. As a result, the asphaltene-rich fraction is discharged from disengagement zone 142 and collected in asphaltene collection zone 145, which is a narrow vessel section of vessel reactor 140. Reactions in disengagement zone 142 can include cracking reactions, dealkylation reactions, isomerization reactions, dehydrogenation reactions, cyclization reactions, aromatization reactions, dimerization reactions, desulfurization reactions, denitrogenation reactions, demetallization reactions, deoxygenation reactions, oxidation reactions, and combinations of the same. Cracking reactions are the primary reaction pathway in disengagement zone 142. Oxidation reactions are caused by slipped oxidizing agent from the asphaltene collection zone.

Oxidizing agent stream 48 is introduced to the bottom of asphaltene collection zone 145. Oxidizing agent stream 48 is introduced through a sparging device, which enables uniform distribution of the oxidizing agent. The sparging device can include a distributer. Oxidizing agent stream 48 can include an oxidizing agent dispersed in water. The oxidizing agent can be any oxygen containing material that can release atomic or molecular oxygen at temperatures greater than 350° C. due to thermal decomposition. Examples of oxidizing agent include hydrogen peroxide, organic peroxide, oxygen gas, air, or combinations of the same. The flow rate of oxidizing agent stream 48 is based on the mass amount of C7-asphaltene content of feedstock 10. The flow rate of oxidizing agent stream 48 is such that the amount of oxygen is in the range of 10% to 300% of the mass amount of C7-asphaltene content, alternately in the range of 50% to 150% of the mass amount of C7-asphaltene content, and alternately in the range of 25% to 100% the mass amount of C7-asphaltene content. Oxidizing agent stream 48 contains water to ensure distribution of oxidizing agent stream 48 in vessel reactor 140. The flow rate of water in oxidizing agent stream 48 is in the range of 100% to 5000% of the oxidizing agent's mass flow rate and alternately in the range of 500% to 2000% of the oxidizing agent's mass flow rate. By way of example, if the mass amount of C7-asphaltene content in feedstock 10 is 25 wt % and the flow rate is 1000 kg/hr, then the flow rate of C7-asphaltene content is 250 kg/hr. The amount of oxygen in the oxidizing agent stream then is between 25 kg/hr and 750 kg/hr. If the oxidizing agent is hydrogen peroxide, the oxygen amount in the oxidizing agent is 47%. If the oxidizing agent is oxygen gas, the oxygen amount in the oxidizing agent is 100%. The pressure of oxidizing agent stream 48 is the same as vessel reactor 140.

The oxidizing agent in oxidizing agent stream 48 oxidizes asphaltenes in the asphaltene-rich fraction to produce a partially oxidized asphaltene fraction. The asphaltene-rich fraction also contains unconverted hydrocarbons. In addition to oxidation reactions, reactions in asphaltene collection zone 145 can include cracking reactions, dealkylation reactions, isomerization reactions, dehydrogenation reactions, cyclization reactions, aromatization reactions, dimerization reactions, desulfurization reactions, denitrogenation reactions, demetallization reactions, deoxygenation reactions, and combinations of the same. The oxidizing agent flows up through asphaltene collection zone 145 to disengagement zone 142 to oxidize the non-asphaltenic fraction to produce carbon monoxide, carbon dioxide, and oxygenates.

Vessel reactor 140 is in the absence of sodium hydroxide. Vessel reactor 140 is in the absence of externally supplied aromatic solvent, paraffinic sulfur, catalyst, hydrogen, sulfuric acid, potassium permanganate, and combinations of the same.

Vessel reactor 140 has two outlets, one in disengagement zone 142 and one in asphaltene collection zone 145.

Reactor upper effluent 50 exits disengagement zone 142 and is introduced to upper cooler 150. Reactor upper effluent 50 contains unconverted hydrocarbons, upgraded hydrocarbons, non-asphaltene fractions, and combinations of the same. The upgraded hydrocarbons include oxygenated hydrocarbons. Oxygenated hydrocarbons include carboxylic acid, ketones, aldehydes, and combinations of the same. Upper cooler 150 can reduce the temperature of reactor upper effluent 50 to produce cooled upper effluent 55. Upper cooler 150 can be any heat exchanger capable of reducing the temperature of reactor upper effluent 50. In at least one embodiment, upper cooler 150 includes a heat exchanger. The temperature of cooled upper effluent 55 is less than the critical temperature of water. In at least one embodiment, the temperature of cooled upper effluent 55 is between 50° C. and 150° C. Cooled upper effluent 55 can be introduced to pressure control unit 155.

Pressure control unit 155 can reduce the pressure of cooled upper effluent 55 to produce upper upgraded stream 60. Pressure control unit 155 can be any type of pressure regulator configured to reduce the fluid pressure of cooled upper effluent 55. Examples of pressure control unit 155 includes a back pressure regulator and a pressure control valve. The pressure of upper upgraded stream 60 for a given temperature is above the pressure at which steam is generated. The pressure of upper upgraded stream 60 is between 1 barg and 5 barg. Pressure control unit 155 regulates the pressure of the entire system. Upper upgraded stream 60 is introduced to product mixer 175.

Reactor bottom effluent 65 exits asphaltene collection zone 145 and is introduced to bottom cooler 160. Reactor bottom effluent 65 contains unconverted hydrocarbons, partially oxidized asphaltene fraction, and combinations of the same. The flow rate of reactor bottom effluent 65 can be controlled by a level valve logically connected to asphaltene collection zone 145 configured to control the level in asphaltene collection zone 145. The level valve can allow reactor bottom effluent 65 to discharge intermittently or continuously depending on the level in asphaltene collection zone 145. Bottom cooler 160 can reduce the temperature of reactor bottom effluent 65 to produce cooled bottom effluent 70. Bottom cooler 160 can be any heat exchanger capable of reducing the temperature of reactor bottom effluent 65. In at least one embodiment, bottom cooler 160 include a heat exchanger. The temperature of cooled bottom effluent 70 is less than the critical temperature of water. In at least one embodiment, the temperature of cooled bottom effluent 70 is between 70° C. and 150° C. Cooled bottom effluent 70 can be introduced to pressure regulator unit 165.

Pressure regulator unit 165 can reduce the pressure of cooled bottom effluent 70 to produce centrifuge feed 75. Pressure regulator unit 165 can be any type of pressure regulator configured to reduce the fluid pressure of cooled bottom effluent 70. Examples of pressure regulator unit 165 includes a back pressure regulator and a pressure control valve. The pressure of centrifuge feed 75 is between 1 barg and 5 barg. Centrifuge feed 75 is introduced to centrifuge 170.

Centrifuge 170 can be any type of separation unit capable of separating liquid phases based on density. The temperature in centrifuge 170 can be between 20° C. and 90° C. The pressure in centrifuge 170 can be between 0 barg and 3 barg. Centrifuge 170 is a centrifuge that separates the less dense phase as centrate stream 80 and the denser phase as rejected phase 85. Rejected phase 85 contains the flocculated asphaltene fraction. Rejected phase 85 can be transferred for further treatment in gasification unit, incineration unit, and asphalt production units. Centrate stream 80 is introduced to product mixer 175.

Product mixer 175 mixes centrate stream 80 and upper upgraded stream 60 to produce mixed upgraded stream 90. Product mixer 175 can be any type of mixing device capable of mixing centrate stream 80 and upper upgraded stream 60. Examples of product mixer 175 can include an ultrasonic device, agitator-equipped vessel, and a tee fitting. The temperature of mixed upgraded stream 90 can be between 20° C. and 100° C. The pressure of mixed upgraded stream 90 can be 0 barg and 3 barg. Mixed upgraded stream 90 can be introduced to three-phase separator 180.

Three-phase separator 180 separates mixed upgraded stream 90 to produce gas product 92, upgraded oil product 94, and water product 96. Three-phase separator 180 can include one or more units capable of separating a stream into gas phase and liquid phase streams. As shown in FIG. 1, three-phase separator can be one unit. The temperature of three-phase separator 180 is maintained between 30° C. and 150° C. and alternately between 60° C. and 90° C. The pressure of three-phase separator is maintained between 0.1 and 3 barg. Gas product 92 can contain oxygen, carbon monoxide, carbon dioxide, hydrogen, water vapor, methane, hydrogen sulfide, and light hydrocarbon gases.

Figure 3:
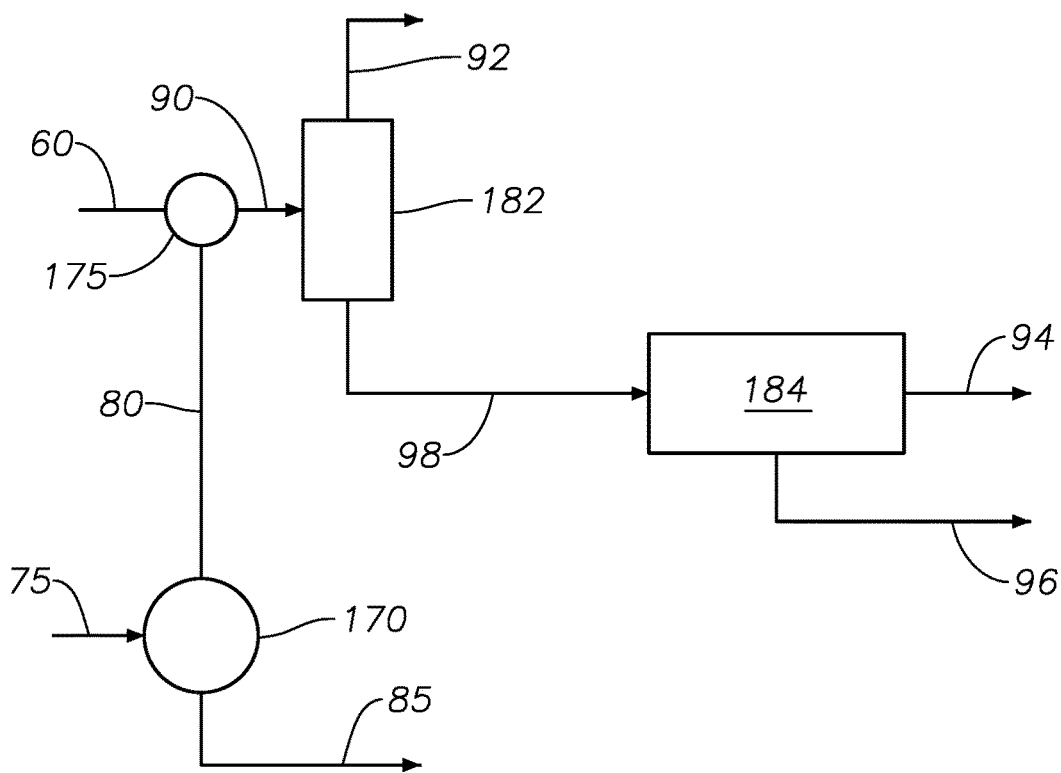
FIG. 3 provides a process diagram of an embodiment of the process.

In an alternate embodiment, as shown in FIG. 3, three-phase separator 180 can include two units gas-liquid separator 182 and oil-water separator 184. In the embodiment described with reference to FIG. 3, mixed upgraded stream 90 is first separated in gas-liquid separator 182 to separate gas product 92 and liquid product 98. Liquid product 98 is then introduced to oil-water separator 184. Oil-water separator 184 separates upgraded hydrocarbons from water by gravitational separation to produce upgraded oil product 94 and water product 96. In certain embodiments, a demulsifier can be added to oil-water separator 184 to enhance separation of water and upgraded hydrocarbons.

Notably in the instant process and system to convert and separate asphaltenes the oxidation of asphaltenes only occurs under supercritical conditions in the presence of supercritical water in the vessel reactor. No oxidation of asphaltenes occurs outside of the vessel reactor. In at least one embodiment, metals are concentrated in the asphaltene-rich fraction and the oxidizing agent reacts with those metals to produce metal oxides and metal hydroxides. The metal oxides and metal hydroxides remain concentrated in the asphaltene-rich fraction and are concentrated in the asphaltene collection zone.

EXAMPLES

Example 1. Example 1 was performed in a pilot scale system based on the process flow diagram of FIG. 1. Feedstock 10 was an atmospheric residue fraction from a crude oil with an API gravity of 14.37, a sulfur content of 3.75 wt %, and a C7-asphaltene content of 6.5 wt %. The true boiling point fractions of feedstock 10 are shown in Table 1.

TABLE 1

True Boiling Point Fractions of the Feedstock in Example 1

| Distillation Yield (% by volume) | Temperature (° C.) |
|---|---|
| 5% | 398 |
| 10% | 422 |
| 30% | 469 |
| 50% | 522 |
| 70% | 578 |
| 90% | 634 |
| 95% | 676 |

Feedstock 10 was at a temperature of 50° C., a pressure of 1 barg, a mass flow rate of 13,481 kg/hr and liquid volume flow rate of 2,100 barrels per day. The temperature and pressure of feedstock 10 were increased to produce heated feedstock 30 at a temperature of 180° C. and a pressure of 270 barg.

Water stream 5 was a demineralized water having a conductivity of a 0.8 µS/cm at 25° C. Water stream 5 was at a temperature of 30° C., a pressure of 1 barg, a flow rate of 19,712 kg/hr and liquid volume flow rate of 2,982 barrels per day. The temperature and pressure of water stream 5 were increased to produce supercritical water 25 at a temperature of 480° C. and a pressure of 270 barg.

Heated feedstock 30 and supercritical water 25 were mixed in feed mixer 120 to produce mixed feed 35 at a temperature of 405° C., pressure of 270 barg, a mass flow rate of 33,193 kg/h. After heating in pre-heater 125, the temperature of reactor feed 40 was 435° C.

Tubular reactor 130 was four pipes arranged in series, each 20 meters long with an inner diameter of 460.4 mm and an outer diameter of 660.4 mm. The four pipes were oriented horizontally and stacked vertically with mixed feed 35 introduced at the pipe highest elevation pipe and reactor effluent exiting from the lowest elevation pipe. The total residence time of the fluid in the pipes is about 3.1 minutes, calculated by assuming the internal fluid is water at the same mass flow rate. The Reynolds number of the internal fluid in the pipes was greater than 10,000, calculated by assuming the internal fluid is water at the same mass flow rate. Each pipe was surrounded by heaters and the temperature was gradually increased in each pipe. The temperature of the fluid at the end of the first pipe was 441° C., the temperature at the end of the second pipe was 448° C., the temperature at the end of the third pipe was 450° C., and the temperature at the end of the fourth pipe was 450° C.

Vessel reactor 140 had an internal volume of 67 m$^3$. The volumetric flow rate was estimated to be 268 m$^3$/hr at the operating conditions in vessel reactor 140, calculated by assuming the internal fluid was water. Disengagement zone 142 had a diameter of 4.9 meters and a height of 3.0 meters. Asphaltene collection zone 145 had a diameter of 2.2 meters and a height of 2.1 meters. Asphaltene collection zone 145 included a distributer to uniformly distribute oxidizing agent stream 48 at the bottom of asphaltene collection zone 145. Oxidizing agent stream 48 included a mass flow rate of 657 kg/hr of oxygen and a mass flow rate of 7,886 kg/hr of water. The oxidizing agent stream was at a temperature of 180° C. and a pressure of 270 barg.

The stream properties downstream of vessel reactor 145 are shown in Table 2.

TABLE 2

Stream Properties

| | Upper Reactor Effluent 50 | Cooled Upper Effluent 55 | Upper Upgraded Stream 60 | Bottom Reactor Effluent 65 | Cooled Bottom Effluent 70 | Centrifuge Feed 75 |
|---|---|---|---|---|---|---|
| Temperature (° C.) | 450 | 90 | 87 | 450 | 90 | 102 |
| Pressure (barg) | 270 | 270 | 2 | 270 | 270 | 2 |
| Mass Flow (kg/h) | 36766 | 36766 | 36766 | 4971 | 4971 | 4971 |

| | Centrate 80 | Rejected Phase 85 | Mixed Upgraded Stream 90 | Gas Product 92 | Upgraded oil Product 94 | Water Product 96 |
|---|---|---|---|---|---|---|
| Temperature (° C.) | 60 | 60 | 85 | 85 | 85 | 85 |
| Pressure (barg) | 2 | 2 | 2 | 2 | 2 | 2 |
| Mass Flow (kg/h) | 2776 | 2195 | 39541 | 2894 | 9440 | 27207 |

Upgraded oil product 94 had an API gravity of 22.5, a sulfur content of 1.43 wt %, and a C7-asphaltene content of 0.12 wt %. Upgraded oil product 94 had the properties shown in Table 3.

TABLE 3

Properties of upgraded oil product 94

| Distillation Yield (% by volume) | Temperature (° C.) |
|---|---|
| 5% | 116 |
| 10% | 165 |
| 30% | 363 |
| 50% | 420 |
| 70% | 468 |
| 90% | 528 |
| 95% | 551 |

Although described in detail, it should be understood that various changes, substitutions, and alterations can be made hereupon without departing from the principle and scope. Accordingly, the scope should be determined by the following claims and their appropriate legal equivalents. There various elements described can be used in combination with all other elements described herein unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art, except when these references contradict the statements made herein.

As used here and in the appended claims, the words "comprise," "has," and "include" and all grammatical variations thereof are each intended to have an open, non-limiting meaning that does not exclude additional elements or steps.

As used here, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope.

That which is claimed is:

1. A method to convert asphaltenes to partially oxidized asphaltenes, the method comprising the steps of:
   increasing a pressure of a feedstock in a feedstock pump to produce a pressurized feedstock, wherein the feedstock comprises greater than 0.1 weight percent of carbon 7-asphaltene (C7-asphaltene) content;
   increasing a temperature of the pressurized feedstock in a feedstock heater to produce a heated feedstock;
   increasing a pressure of a water stream in a water pump to produce a pressurized water stream;

increasing a temperature of the pressurized water stream in a water heater to produce a supercritical water;

mixing the heated feedstock and the supercritical water in a feed mixer to produce a mixed feed, wherein a temperature of the mixed feed is between 100° C. and 400° C.;

increasing a temperature of the mixed feed in a pre-heater to produce a reactor feed;

treating the reactor feed in a tubular reactor to produce a reactor effluent, wherein the tubular reactor comprises one or more pipes in series, wherein the temperature in the tubular reactor is between 374° C. and 500° C., wherein the pressure is between 220 barg and 330 barg, wherein the residence time is between 0.5 minutes and 30 minutes;

introducing the reactor effluent to a disengagement zone of a vessel reactor, wherein an asphaltene-rich fraction disengages from a non-asphaltene fraction and flows to an asphaltene collection zone of the vessel reactor, wherein the disengagement zone is positioned at a greater elevation than the asphaltene collection zone, wherein the asphaltene-rich fraction comprises asphaltenes;

introducing an oxidizing agent stream to the asphaltene collection zone of the vessel reactor, wherein the oxidizing agent stream comprises an oxidizing agent and water;

reacting the asphaltenes in the asphaltene-rich fraction with oxygen from the oxidizing agent to produce partially oxidized asphaltenes, wherein a temperature in the vessel reactor is in the range between 374° C. and 500° C., wherein a pressure in the vessel reactor is between 220 barg and 330 barg;

withdrawing an upper reactor effluent from the disengagement zone;

withdrawing a bottom reactor effluent from the asphaltene collection zone;

reducing a temperature of the upper reactor effluent in an upper cooler to produce a cooled upper effluent, wherein the temperature of the cooled upper effluent is between 50° C. and 150° C.;

reducing a pressure of the cooled upper effluent in a pressure control unit to produce an upper upgraded stream, wherein the pressure of the upper upgraded stream is between 1 barg and 5 barg;

reducing a temperature of the bottom reactor effluent in a bottom cooler to produce a cooled bottom effluent, wherein the temperature of the cooled bottom effluent is between 70° C. and 150° C.;

reducing a pressure of the cooled bottom effluent in a pressure regulator unit to produce a centrifuge feed, wherein the pressure of the centrifuge feed is between 1 barg and 5 barg;

separating the centrifuge feed in a centrifuge to produce a centrate and a rejected phase, wherein the temperature in the centrifuge is between 20° C. and 90° C., wherein the rejected phase comprises flocculated asphaltenes, wherein the flocculated asphaltenes comprise partially oxidized asphaltenes;

mixing the centrate and the upper upgraded stream in a product mixer to produce a mixed upgraded stream; and separating the mixed upgraded stream in a three-phase separator to a produce gas product, an upgraded oil product, and a water product.

2. The method of claim 1, wherein a temperature of the heated feedstock is between between 100° C. and 250° C. and a pressure is between 220 barg and 330 barg.

3. The method of claim 1, wherein a temperature of the supercritical water is between 374° C. and 600° C. and a pressure is between 220 barg and 330 barg.

4. The method of claim 1, wherein the oxidizing agent is selected from the group consisting of hydrogen peroxide, organic peroxide, oxygen gas, air, or combinations of the same.

5. The method of claim 1, wherein the tubular reactor comprises 4 pipes in series.

6. The method of claim 1, wherein a flow rate of oxidizing agent stream is such that an amount oxygen is in the range of 10% to 300% of the mass amount of C7-asphaltene content.

7. The method of claim 1, wherein the total volume of the vessel reactor is equal to 0.1 to 1 times the volumetric flow rate of the reactor effluent.

8. The method of claim 1, wherein the ratio of the volume of the disengagement zone to the volume of the asphaltene collection zone is between 1:1 and 10:1.

9. The method of claim 1, wherein the ratio of the diameter of the disengagement zone to the volume of the asphaltene collection zone is between 2:1 and 5:1.

10. A system to convert asphaltenes to partially oxidized asphaltenes, the system comprising:

a feedstock pump configured to increase a pressure of a feedstock to produce a pressurized feedstock, wherein the feedstock comprises greater than 0.1 weight percent of carbon 7-asphaltene (C7-asphaltene) content;

a feedstock heater fluidly connected to the feedstock pump, the feedstock heater configured to increase a temperature of the pressurized feedstock to produce a heated feedstock;

a water pump configured to increase a pressure of a water stream to produce a pressurized water stream;

a water heater fluidly connected to the water pump, the water heater configured to produce a supercritical water;

a feed mixer fluidly connected to the feedstock heater and the water heater, the feed mixer configured to mix the heated feedstock and the supercritical water to produce a mixed feed, wherein the feed mixer is selected from the group consisting of an ultrasonic device, agitator-equipped vessel, and a tee fitting;

a pre-heater fluidly connected to the feed mixer, the pre-heater configured to produce a reactor feed;

a tubular reactor fluidly connected to the pre-heater, the tubular reactor configured to produce a reactor effluent, wherein the tubular reactor comprises one or more pipes in series, wherein the tubular reactor has a residence time between 0.5 minutes and 30 minutes;

a vessel reactor fluidly connected to the tubular reactor, the vessel reactor configured to produce an upper reactor effluent and a bottom reactor effluent, wherein the vessel reactor comprises a disengagement zone and an asphaltene collection zone, wherein the disengagement zone is positioned at a greater elevation than the asphaltene collection zone, wherein a distributer in the asphaltene collection zone is configured to distribute oxidizing agent stream into the asphaltene collection zone, wherein the oxidizing agent stream comprises oxidizing agent and water;

an upper cooler fluidly connected to the disengagement zone, the upper cooler configured to produce a cooled upper effluent;

a pressure control unit fluidly connected to the upper cooler, the pressure control unit configured to produce an upper upgraded stream;

a bottom cooler fluidly connected to the asphaltene collection zone, the bottom cooler configured to produce a cooled bottom effluent;

a pressure regulator unit fluidly connected to the bottom cooler, the pressure regulator unit configured to produce a centrifuge feed;

a centrifuge fluidly connected to the pressure regulator unit, the centrifuge configured to produce a centrate and a rejected phase;

a product mixer fluidly connected to the pressure control unit and the centrifuge, the product mixer configured to mix the upper upgraded stream and the centrate to produce a mixed upgraded stream; and a three-phase separator fluidly connected to the product mixer, the three-phase separator configured to produce a gas product, an upgraded oil product, and a water product.

11. The system of claim 10, wherein a temperature of the heated feedstock is between between 100° C. and 250° C. and a pressure is between 220 barg and 330 barg.

12. The system of claim 10, wherein a temperature of the supercritical water is between 374° C. and 600° C. and a pressure is between 220 barg and 330 barg.

13. The system of claim 10, wherein the oxidizing agent is selected from the group consisting of hydrogen peroxide, organic peroxide, oxygen gas, air, or combinations of the same.

14. The system of claim 10, wherein the tubular reactor comprises 4 pipes in series.

15. The system of claim 10, wherein a flow rate of oxidizing agent stream is such that an amount oxygen is in the range of 10% to 300% of the mass amount of C7-asphaltene content.

16. The system of claim 10, wherein the total volume of the vessel reactor is equal to 0.1 to 1 times the volumetric flow rate of the reactor effluent.

17. The system of claim 10, wherein the ratio of the volume of the disengagement zone to the volume of the asphaltene collection zone is between 1:1 and 10:1.

18. The system of claim 10, wherein the ratio of the diameter of the disengagement zone to the volume of the asphaltene collection zone is between 2:1 and 5:1.

* * * * *